United States Patent [19]

Veber et al.

[11] Patent Number: 5,457,177
[45] Date of Patent: Oct. 10, 1995

[54] THROMBIN RECEPTOR RADIOLIGANDS

[75] Inventors: Daniel F. Veber, Ambler; Ruth F. Nutt, Green Lane; Dong-mei Feng, Harleysville; Robert J. Gould, Green Lane; Thomas M. Connolly, Harleysville, all of Pa.

[73] Assignee: Merck & Co., Inc., Rahway, N.J.

[21] Appl. No.: 77,850

[22] Filed: Jun. 16, 1993

[51] Int. Cl.⁶ .............................. C07K 7/06; A61K 38/08
[52] U.S. Cl. .................................................. 530/329
[58] Field of Search ............................ 530/329; 514/17, 514/5

[56] References Cited

U.S. PATENT DOCUMENTS 5,192,747  3/1993  Krstenansky ............................... 514/15
5,279,812  1/1994  Krstenansky ............................. 424/1.1

FOREIGN PATENT DOCUMENTS

92/14750  3/1992  WIPO .

OTHER PUBLICATIONS

J. Biol. Chemistry, Platelet Glycocalicin vol. 263, No. 10, pp. 3435–3443, T. Okumura et al.
J. of Biol. Chem., The Binding of Thrombin to the Surface of Human Platelets, vol. 249, No. 8 pp. 2646–2651, 1974, Tollefsen et al.
Cell., Molecular Cloning of a Functional Thrombin . . . , vol. 64, pp. 1057–1068, Mar. 22, 1991, Thien–Khai H. Vu et al.
J. of Biol. Chemistry, Thrombin Interaction with Platelets, vol. 262, No. 7 pp. 3030–3036 (1987), Gronke et al.
J. of Biol. Chem., Structure–Function Relations in the Interaction of alpha–Thrombin with Blood Platelets, vol. 252, No. 20, 7118–7123 (1977), Workman et al.
Biochemical & Biophysical Research Commun., Minimal Sequence Requirement of Thrombin Receptor Agonist Peptide, vol. 184, No. 2 pp. 790–796 (1992), Kwan Y. Hui et al.
J. of Biol. Chem., Communication, vol. 267, No. 19, Jul., pp. 13146–13149, Scarborough et al.
J. of Biol. Chem., "Structure–Function Relationships in the Activation of Platelet Thrombin Receptors by Receptor–derived Peptides", vol. 267, No. 9, pp. 6081–6085, 1992, Vassallo et al.
Organic & Medicinal Chemistry Letters, alpha–Hydroxy–and alpha–Ketoester Functionalized Thrombin Inhibitors, vol. 2, No. 12, pp. 1607–1612, Iwanowicz et al.
J. Am. Chem. Soc., Design, Synthesis and Kinetic Evaluation of a Unique Cladd of Elastase Inhibitors . . . , 114, 1854–1863, Edwards et al.
Thrombos, Diathes, haemorth. (Stuttg.). Thrombin Interaction with Human Platelets . . . 1974, 32, 207, David R. Phillips.
Chapter 3, Dept. of Biochemistry, St. Jude Children's Research Hospital, Platelet membrane proteins:composition and receptor function, Berndt and Phillips.
Biochemistry, Platelet Stimulation by Thrombin and Other Proteases, vol. 14, No. 6, 1975, Martin et al.
Blood, PPack–thrombin Inhibits Thrombin–Induced Platelet Aggregation . . . vol. 75, No. 10 1990, pp. 1983–1990, Greco et al.
The Embo Journal, The refined 1.9 A crystal structure of human alpha–thrombin . . . , vol. 8, No. 11 pp. 3467–3475, Bode et al.
Scarborough et al., J. Biol. Chem. 267 (19) pp. 13146–13149 (1992) (IDS).
Vassallo et al., J. Biol. Chem. 267(9) pp. 6081–6085 (1992).
Assoian et al., Anal. Biochem. 103 70–76 (1980).

*Primary Examiner*—Jill Warden
*Assistant Examiner*—Carol A. Salata
*Attorney, Agent, or Firm*—Richard S. Parr; Melvin Winokur

[57] ABSTRACT

The radioligands are six amino acid peptides having iodinated tyrosine at amino acid position six, including Ala-pFPhe-hArg-Cha-hArg-Tyr(I)-NH₂, which mimic the activated form of the thrombin receptor protein. Thrombin receptor radioligands of the present invention are useful for screening for thrombin receptor antagonists.

5 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
    ( A ) LENGTH: 6
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:1:

Ala Xaa Arg Xaa Xaa Xaa
1               5

( 2 ) INFORMATION FOR SEQ ID NO:2:

( i ) SEQUENCE CHARACTERISTICS:
    ( A ) LENGTH: 6
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:2:

Ala Xaa Arg Xaa Xaa Xaa
1               5

( 2 ) INFORMATION FOR SEQ ID NO:3:

( i ) SEQUENCE CHARACTERISTICS:
    ( A ) LENGTH: 6
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:3:

Ala Xaa Xaa Xaa Xaa Xaa
1               5

( 2 ) INFORMATION FOR SEQ ID NO:4:

( i ) SEQUENCE CHARACTERISTICS:
    ( A ) LENGTH: 6
    ( B ) TYPE: amino acid
    ( C ) STRANDEDNESS: unknown
    ( D ) TOPOLOGY: unknown ( i i ) MOLECULE TYPE: peptide ( x i ) SEQUENCE DESCRIPTION: SEQ ID NO:4:

Ala Xaa Xaa Xaa Xaa Xaa
1               5

( 2 ) INFORMATION FOR SEQ ID NO:5:

( i ) SEQUENCE CHARACTERISTICS:

(A) LENGTH: 6
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:5:

Ala Xaa Xaa Xaa Xaa Tyr
 1           5

THROMBIN RECEPTOR RADIOLIGANDS

BACKGROUND OF THE INVENTION

Thrombin is a powerful factor in regulating the state of the cardiovascular system. It is clear that thrombin is an integral component involved in the formation of blood clots by catalyzing the conversion of fibrinogen to fibrin, which is an integral pan of most clots. In addition, thrombin is known to act directly on cells in the blood and in the interior blood vessel wall, and specifically to activate platelets to form clots. Thrombin-induced platelet activation is particularly important for arterial thrombus formation, a process that causes myocardial infarction and some forms of unstable angina and stroke. In addition, thrombin promotes intimation and other cellular activities. Thrombin is chemotactic for monocytes, mitogenic for lymphocytes, and causes endothelial cells to express the neutrophil adhesive protein GMP-140 on their surfaces and inhibits the growth of these cells. Thrombin elicits platelet-derived growth factor from the endothelium and is a mitogen for mesenchymal cells.

Because thrombin is capable of direct activation of cells, it is assumed that at least one thrombin receptor exists. However, it has not been possible to detect the presence of a thrombin receptor by traditional binding studies, since thrombin is capable of binding a large number of sites present on cells which do not directly mediate the cellular responses to thrombin, and thus the background levels of binding are prohibitively high.

The thrombin-binding proteins that have been identified do not seem to function as transduction molecules (Gronke, R. S. et al., *J Biol Chem* (1987) 262:3030-3036; Okamura, T., et al., *J Biol Chem* (1978) 253:3435). Modified thrombins that are physiologically inactive seem to bind to platelets in the same way as thrombin itself. Thus, the binding sites identified by traditional binding studies may not be related to functional thrombin receptors. Also, since thrombin is a protease, if the receptor were proteolytically cleaved by its interaction with thrombin, the receptor's ability to bind tightly to thrombin would be decreased. All of the foregoing factors suggest that traditional binding studies in an effort to identify and characterize a thrombin receptor might ultimately be unproductive.

While it has been assumed that a thrombin receptor exists, no direct experimental evidence exists from the studies conducted so far, whether proteolytic cleavage by thrombin is involved in its receptor activation. When thrombin is treated with reagents which covalently modify and render it proteolytically inactive, its ability to stimulate platelets is abolished (Bemdt, M. C., et al., "Platelets in Biology and Pathology" (1981) Elsevier/North Holland Biomedical Press, pp. 43–74; Martin, B. M., et al., *Biochemistry* (1975) 14:1308-1314; Tollefsen, D. M., et al., *J Biol Chem* (1974) 249:2646-2651; Phillips, D. R., *Thrombin Diath Haemorrh* (1974) 32:207-215; Workman, E. F., et al., *J. Biol Chem* (1977) 252:7118-7123; Greco, N. J., et al., *Blood* (1990) 75:1983-1990). The modified forms of thrombin described in the reports above contain bulky or charged moieties that occupy the active site and also obscure additional regions of the surface of thrombin that bind substrate (Bode, W., et al., *Embo J* (1989) 8:3467-3475). Some of the chemically-modified thrombins do not, in fact, block thrombin-induced platelet activation.

Coughlin, et al., WO 9214750, describes cloning and sequencing of DNA encoding the cell surface receptor for thrombin, and recombinant production of the thrombin receptor at cell surfaces. Assay systems for the detection of thrombin and the evaluation of thrombin agonists and antagonists are described.

SUMMARY OF THE INVENTION

Thrombin receptor radioligands of the present invention are useful for screening for antagonists of thrombin receptor activation. The radioligands are potent (<100 nM) and therefore particularly useful in large volume screening of potential thrombin receptor antagonists. Antagonists of thrombin receptor activation are useful as antithrombotic agents. Thus, the invention includes both thrombin receptor radioligands defined below and a thrombin receptor binding assay using the radioligands, for identifying thrombin receptor antagonists.

In addition to the high potency of these radioligands, the radioligands have specific chemical sites for introduction of the radiolabel to produce a radio receptor assay.

The radioligands are peptides having at least six amino acids and falling within the following general structure:

A-B-C-D-E-F-Z wherein

A=Thr, Ser, Ala, or Gly;

B=Phe or halogenated Phe;

C, when F is Tyr(I) or Tyr($I_2$),=Leu, Val, Cha, Nle, Phe, Arg, hArg, or Lys;

C, when F is Tyr,=NH—CH(R)CO—, t,0040
wherein n=2, 3, or 4;

D=Leu or Cha;

E=Arg, hArg, or Lys;

F=Tyr, Tyr(I), or Tyr($I_2$); and

Z=OH, $OCH_3$, or NRR', wherein RR'=H, alkyl, aryl, or 1–15 amino acids.

The invention also includes a procedure for identifying thrombin receptor antagonists among thrombin receptor antagonist candidates, and determining thrombin receptor antagonist activity using the above-described radioligands.

DETAILED DESCRIPTION OF THE INVENTION

The invention includes thrombin receptor radioligands which mimic the human thrombin receptor, and methods for determining thrombin receptor antagonist activity. The method comprises:

(a) isolating and washing human platelets or human platelet membranes, (b) incubating a combination of platelets or platelet membranes with a thrombin receptor radioligand and a candidate thrombin receptor antagonist, (c) cooling the incubated combination by adding cold sodium chloride, (d) filtering and washing the coiled incubated combination, and (e) measuring bound radioactivity.

Preferably, the thrombin receptor radioligand is selected from the group of compounds consisting of:

Ala-pFPhe-Arg-Cha-hArg-Tyr(I)-$NH_2$,

Ala-pFPhe-Arg-Cha-hArg-Tyr($I_2$)-$NH_2$,

Ala-pFPhe-hArg-Cha-hArg-Tyr(I)-NH$_2$,

Ala-pFPhe-hArg-Cha-hArg-Tyr(I$_2$)-NH$_2$, and t,0070

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal H$^+_2$ and C-terminal O$^-$ at physiological pH are understood to be present though not necessarily specified and shown, either in specific examples or in genetic formulas. Free functional groups on the side chains of the amino acid residues can also be modified by amidation, acylation or other substitution, which can, for example, change the solubility of the compounds without affecting their activity.

In the peptides shown, each residue, where appropriate, is represented by a one or three letter designation, corresponding to the trivial name of the amino acid, in accordance with the following conventional list: t,0090

In the specific peptides shown in the present application, the L-form of any amino acid residue having an optical isomer is intended unless the D-form is expressly indicated.

Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows:

Acidic: Aspartic acid and Glutamic acid;

Basic/noncyclic: Arginine, Lysine;

Basic/cyclic: Histidine;

Neutral/polar/small: Glycine, serine, cysteine;

Neutral/nonpolar/small: Alanine;

Neutral/polar/large/nonaromatic: Threonine, Asparagine, Glutamine;

Neutral/polar/large aromatic: Tyrosine;

Neutral/nonpolar/large nonaromatic: Valine, Isoleucine, Leucine, Methionine;

Neutral/nonpolar/large/aromatic: Phenylalanine, and Tryptophan.

The secondary amino acid proline, although technically within the group neutral/nonpolar/large/cyclic and nonaromatic, is a special case due to its known effects on the secondary conformation of peptide chains, and is not, therefore, included in this defined group.

Non-natural, uncommon amino acids, include, for example, beta-alanine (beta-Ala), or other omega-amino acids, such as 3-amino propionic, 4-amino butyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); β-2-thienylalanine (Thi); and methionine sulfoxide (MSO). These also fall conveniently into particular categories.

Based on the above definitions,

Sar and beta-Ala and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/ large/nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4aminobutyric) or large (all others).

Other amino acid substitutions can also be included in peptide compounds within the scope of the invention and can be classified within this general scheme according to their structure.

All of the compounds of the invention, when an amino acid forms the C-terminus, may be in the form of the pharmaceutically acceptable salts or esters. Salts may be, for example, Na$^+$, K$^+$, Ca$^{+2}$, Mg$^{+2}$ and the like; the esters are generally those of alcohols of 1–6C.

Assays

Experiments were carded out to screen for the potency of thrombin receptor-derived peptides and to identify receptor antagonists.

Assay to determine EC$_{50}$ values for peptides

Human platelets are isolated and washed as described in Connolly et al. (1992) *J. Biol. Chem.* 267, 6893–6898 and suspended at 2 ×10$^8$ platelets/ml in a modified Tyrode's buffer without Ca$^{++}$. Platelets are incubated with 0.2 mg/ml human fibrinogen for 2 minutes at 37° C. The sample is transferred to an aggregometer, stirred, the test compound is added and aggregation monitored for 5 min. The extent and rate of aggregation is calculated by the Agglink Software program supplied by Chronolog Corp. $EC_{50}$ values are visually determined from plots of the extent and rate of aggregation versus log concentration of test compound. The mean of these values from 3 separate experiments performed on blood from different donors on different days is reported in μM.

Assay used to determine antagonist activity

Radioligand Binding Assay -(A) Preparation of radioligand Unlabeled peptide is iodinated using the IODO-GEN radioiodination reagent together with [$^{125}$I]NaI. The non iodinated, mono and diiodinated species are separated by $C_{18}$ reverse phase HPLC chromatography. The final specific activities were between 60 and 570 Ci/mmole. (B) Human platelets are isolated and washed as above. Platelets are incubated with radioligand [$^{125}$I]-peptide alone or in the presence of thrombin receptor antagonist in a final volume of 250–500 μl for 10–60 min at 4°, 22° or 37° C. The binding assay is terminated by the addition of ice cold 0.15 M NaCl followed by filtration on Whatman GF/C filters that had been presoaked in 0.3 % polyethylenimine. The filters are washed 3 more times with ice cold buffer and the bound radioactivity on the filters monitored. Antagonist activity is noted as a decrease in counts bound as compared to the control radioligand bound. (C) Human platelet membranes prepared according to Biochim. et Biophys Act (1986) 854, 67–76, made up in 50mM Tris HCL, pH 7.6, 1 mM EGTA, 10 mM $MgCl_2$, 62–250 μg assay, are incubated as with platelets above. The remainder of the procedure is as with the platelets.

Preferred radioligands of the present invention are hexapeptides having $EC_{50}$(μM) values <0.1 μM. $EC_{50}$ values, expressed in micromolar units, represent the concentration of measured compound required to elicit a 50% maximal aggregation according to the platelet aggregation assay. These radioligands are particularly useful for quickly identifying thrombin receptor antagonists.

The thrombin receptor ligands mimic the activated form of the thrombin receptor protein and are useful in encouraging platelet aggregate formation in localized application. They also stimulate fibroblast proliferation and thus may be useful in promoting wound healing.

Specifically preferred radioligands, referenced by Sequence ID Number, are the following hexapeptides: t,140 wherein pFPhe is para-fluorophenylalanine, hArg is homoarginine, Cha is cyclohexylalanine, I is iodine, Tyr(I) is monoiodinated tyrosine, and Tyr($I_2$) is diiodinated tyrosine.

Specifically preferred assays for identifying thrombin receptor antagonists are those described below which use the specifically preferred radioligands.

Ligand Preparation

The nonradioactive radioligands of the present invention are prepared by standard solid phase methodology (Merrifield, *J. Am. Chem. Soc.*, 85, 2149 (1964) and Stewart and Young, "Solid Phase Peptide Synthesis", Pierce Chemical Company, Rockford, Ill. (1984)), starting with a methylbenzhydrylamine resin (MBHR). The resin, R, is acylated with a protected amino acid (X') and the α-amino group is deprotected, neutralized and acylated with the next amino acid in the desired sequence. In this manner, the desired peptide-resin A'-B'-C'-D'-E'-F'-MBHR is built. The peptide is cleaved from the solid support using HF-anisole (9:1) and the crude product is isolated by preparative HPLC. Radiolabeled amino acids are treated, e.g. with an iodinating reagent, prior to solid phase synthesis. In general, the procedure for preparing radioligands is represented by the following scheme: t,160
DMF is dimethylformamide, and HF is hydrogen fluoride.

EXAMPLE 1

Method for identifying thrombin receptor antagonists

Unlabeled peptide t,170
prepared according to the procedures generally outlined above, is iodinated using the IODO-GEN radioiodination reagent together with [$^{125}$I]NaI, to form t,171
The non iodinated, mono and diiodinated species are separated by $C_{18}$ reverse phase HPLC chromatography. The final specific activities were between 60 and 570 Ci/mmole.

Human platelets are isolated and washed as above. Platelets are incubated with radioligand [$^{125}$I]-peptide alone or in the presence of thrombin receptor antagonist in a final volume of 500 μl for 30 min at 22° C. The binding assay is terminated by the addition of ice cold 0.15 M NaCl followed by filtration on Whatman GF/C filters that had been presoaked in 0.3 % polyethylenimine. The filters are washed 3 more times with ice cold buffer and the bound radioactivity on the filters monitored.

Antagonist activity is noted as a decrease in counts bound as compared to the control radioligand bound.

EXAMPLE 2

Method for identifying thrombin receptor antagonists

Unlabeled peptide

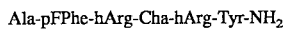
Ala-pFPhe-hArg-Cha-hArg-Tyr-NH$_2$ prepared according to the procedures generally outlined above, is iodinated using the IODO-GEN radioiodination reagent together with [$^{125}$I]NaI, to form

Ala-pFPhe-hArg-Cha-hArg-Tyr(I)-NH$_2$.

The non iodinated, mono and diiodinated species are separated by $C_{18}$ reverse phase HPLC chromatography. The final specific activities were between 60 and 570 Ci/mmole.

Human platelets are isolated and washed as above. Platelets are incubated with radioligand [$^{125}$I]-peptide alone or in the presence of thrombin receptor antagonist in a final volume of 500 μl for 30 min at 22° C. The binding assay is terminated by the addition of ice cold 0.15 M NaCl followed by filtration on Whatman GF/C filters that had been presoaked in 0.3% polyethylenimine. The filters are washed 3 more times with ice cold buffer and the bound radioactivity on the filters monitored. Antagonist activity is noted as a decrease in counts bound as compared to the control radioligand bound.

Thrombin receptor antagonists—therapeutic uses

The thrombin receptor antagonists identified using the assay described above can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent.

The thrombin receptor antagonists may be administered to patients where prevention of thrombosis by thrombin inhibition is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. They may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. The thrombin receptor antagonists may be administered to prevent adhesion.

Other applications of the thrombin receptor antagonists include prevention of platelet thrombosis, thromboembolism and reocclusion during and after thrombolytic therapy and prevention of platelet thrombosis, thromboembolism and reocclusion after angioplasty or coronary and other arteries and after coronary artery bypass procedures. They may also be used to prevent myocardial infarction and unstable angina.

The dosage regimen utilizing the thrombin receptor antagonists is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin receptor antagonists, when used for the indicated effects, will range between about 0.01 mg per kg of body weight per day (mg/kg/day) to about 100 mg/kg/day and preferably 1.0–100 mg/kg/day and most preferably 1–20 mg/kg/day. Intravenously, the most preferred doses will range from about 1 to about 10 mg/kg/minute during a constant rate infusion. Advantageously, the thrombin receptor antagonists may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin receptor antagonists are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin receptor antagonists can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin receptor antagonists may also be delivered by the use of monoclonal antibodies as individual carriers to which the compound molecules are coupled. The thrombin receptor antagonists may also be coupled with soluble polymers as targetable drug carders. Such polymers can include polyvinlypyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the thrombin receptor antagonists may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The thrombin receptor antagonists can also be co-administered with suitable anti-coagulation agents or thrombolytic agents such as plasminogen activators or streptokinase to achieve synergistic effects in the treatment of various ascular pathologies. They may also be combined with heparin, aspirin, or warfarin.

The thrombin receptor antagonists may be used for inhibiting integrin protein-complex function relating to cell attachment activity. They may be administered to patients where inhibition of human or mammalian platelet aggregation or adhesion is desired.

The thrombin receptor antagonists are eliminated from circulation rapidly and are particularly useful in inhibiting platelet aggregation in situations where a strong antithrombotic of short duration or effectiveness is needed. Thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. The thrombin receptor antagonists may be administered to these surgical patients to prevent the formation of thrombi and thromboemboli.

What is claimed is:

1. A peptide selected from the group consisting of

Ala-pFPhe-Arg-Cha-hArg-Tyr($^{125}$I)-NH$_2$,

Ala-pFPhe-Arg-Cha-hArg-Tyr($^{125}$I$_2$)-NH$_2$,

Ala-pFPhe-hArg-Cha-hArg-Tyr($^{125}$I)-NH$_2$,

Ala-pFPhe-hArg-Cha-hArg-Tyr($^{125}$I$_2$)-NH$_2$.

2. A peptide of claim 1 which is

Ala-pFPhe-Arg-Cha-hArg-Tyr(I)-NH$_2$.

3. A peptide of claim 1 which is

Ala-pFPhe-Arg-Cha-hArg-Tyr(I$_2$)-NH$_2$.

4. A peptide of claim 1 which is

Ala-pFPhe-hArg-Cha-hArg-Tyr(I)-NH$_2$.

5. A peptide of claim 1 which is

Ala-pFPhe-hArg-Cha-hArg-Tyr(I$_2$)-NH$_2$.

* * * * *

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

Page 1 of 6

It is certified that error appears in the above-indentified patent and that said Letters Patent is hereby corrected as shown below:

In column 2, line 31, delete "t,0040" and insert

-- wherein R =   $(CH_2)_nNHCO(CH_2)_2-C_6H_3IO$,
$(CH_2)_nNHCO(CH_2)_2-C_6H_4IO$,
$CH_2-C_6H_4IO$, or
$CH_2-C_6H_3I_2O$, --.

In column 3, line 5, delete "t,0070" and insert

--

Ala-pFPhe-Lys-Cha-hArg-Tyr-NH$_2$.

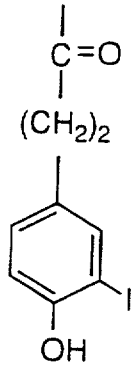

--.

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

It is certified that error appears in the above-indentified patent and that said Letters Patent is hereby corrected as shown below: In column 3, line 26, delete "t,0090" and insert

--

| Amino Acid | Symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

-- .

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

It is certified that error appears in the above-indentified patent and that said Letters Patent is hereby corrected as shown below:

In column 5, line 49, delete "t,140" and insert

--

|  | $EC_{50}$ (µM) | SEQUENCE |
|---|---|---|
| Ala-pFPhe-Arg-Cha-hArg-Tyr(I)-$NH_2$ | 0.030 | 1 |
| Ala-pFPhe-Arg-Cha-hArg-Tyr($I_2$)-$NH_2$ | 0.150 | 2 |
| Ala-pFPhe-hArg-Cha-hArg-Tyr(I)-$NH_2$ | 0.025 | 3 |
| Ala-pFPhe-hArg-Cha-hArg-Tyr($I_2$)-$NH_2$ | 0.090 | 4 |
| Ala-pFPhe-Lys-Cha-hArg-Tyr-$NH_2$ | - | 5 |

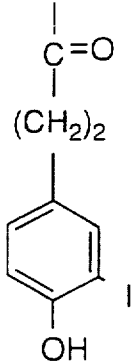

--

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

Page 4 of 6

It is certified that error appears in the above-indentified patent and that said Letters Patent is hereby corrected as shown below: In column 6, line 9, delete "t,160" and insert (MBHR)

1) F'-OH, DCCI

2) TFA/CH$_2$Cl$_2$

3) DIEA/DMF

steps 1-3 with E'. D'. C'. B'. A'

HF-anisole

A-B-C-D-E-F-NH$_2$

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

It is certified that error appears in the above-indentified patent and that said Letters Patent is hereby corrected as shown below:

In column 6, line 19, delete "t,170" and insert

--

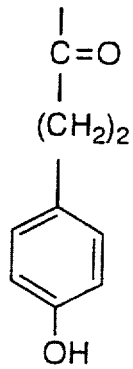

-- .

UNITED STATES PATENT AND TRADEMARK OFFICE
CERTIFICATE OF CORRECTION

PATENT NO. : 5,457,177
DATED : Oct. 10, 1995
INVENTOR(S) : Veber, et al

It is certified that error appears in the above-indentified patent and that said Letters Patent is hereby corrected as shown below:

In column 6, line 22, delete "t,171" and insert --

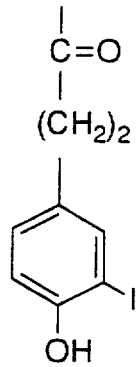

Signed and Sealed this

Sixteenth Day of January, 1996

Attest:

BRUCE LEHMAN

Attesting Officer

Commissioner of Patents and Trademarks